United States Patent [19]

West

[11] Patent Number: 5,145,983
[45] Date of Patent: Sep. 8, 1992

[54] PREPARATION OF N-ACYLIMIDAZOLES

[75] Inventor: Michael West, Wilmington, Del.

[73] Assignee: E. I. Du Pont de Nemours and Company, Wilmington, Del.

[21] Appl. No.: 695,157

[22] Filed: May 3, 1991

[51] Int. Cl.$^5$ ............................................. C07D 233/60
[52] U.S. Cl. ................................................... 548/341
[58] Field of Search .......................................... 548/341

[56] References Cited

PUBLICATIONS

Cram et al., *Organic Chemistry*, pp. 75–78 (1959).
H. A. Staab, Angew. Chem. Intl. Ed., vol. 1, pp. 351–367 (1962).

*Primary Examiner*—Patricia L. Morris
*Assistant Examiner*—Lenora Miltenberger

[57] ABSTRACT

A process for the production of N-acylimidazoles by the reaction of a carboxylic anhydride with carbonyldiimidazole is disclosed. The products are useful as chemical intermediates.

19 Claims, No Drawings

PREPARATION OF N-ACYLIMIDAZOLES

BACKGROUND OF THE INVENTION

1. Field of the Invention

A process for the production of N-acylimidazoles by the reaction of a carboxylic anhydride with a carbonyldiimidazole is disclosed. The products are useful as chemical intermediates.

2. Technical Background

H. A. Staab, Angew. Chem. Intl. Ed., vol. 1, pp. 351-367 (1962) describes various syntheses and uses for N-acylimidazoles (called therein "imidazolides"). At pp. 355-56 the reaction of carbonyldiimidazoles with carboxylic acids, to give one mole of N-acylimidazole, one mole of $CO_2$ and one mole of imidazole per mole of starting material is described. No mention is made in this article of reacting carboxylic anhydrides with a carbonyl-diimidazole to form N-acylimidazoles.

It is the object of the present invention to provide a simple method for the preparation of N-acylimidazoles which gives only easily removable $CO_2$ as a byproduct, and fully utilizes all of the imidazole groups in the carbonyldiimidazole (all of the imidazole groups become N-acylimidazole).

SUMMARY OF THE INVENTION

This invention concerns a process for the production of N-acylimidazoles, comprising, contacting a carboxylic anhydride with a carbonyldiimidazole.

DETAILS OF THE INVENTION

This invention concerns the production of N-acylimidazoles by the reaction of a carboxylic anhydride with a carbonyldiimidazole (herein sometimes abbreviated CDI). The carbonyldiimidazole has the formula

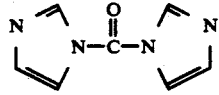

The imidazole rings of the carbonyldimidazole (and the resulting acylimidazole) may be substituted in the 2, 4 or 5 position. It is preferred that in the carbonyldiimidazole both imidazole rings are unsubstituted, that is the compound 1,1'-carbonyldimidazole. By the term N-acylimidazole is meant a compound of the type

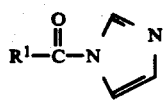

wherein an acyl group is bound to the 1 position of an imidazole ring. The group $R^1$ is hydrocarbyl, which may be substituted with various substituents. The various substituents on the imidazole ring or attached to the group $R^1$ should be inert under process conditions.

The group $R^1$ is derived from the carboxylic anhydride used in the process. Carboxylic anhydrides are well known to those skilled in the art and contain the group $—C(O)—O—C(O)—$, where the free bonds are to hydrocarbyl or substituted hydrocarbyl groups, such as the group $R^1$. Carboxylic anhydrides may be cyclic or acyclic. Thus the carboxylic anhydride may have the formula $R^1C(O)—O—C(O)R^1$, wherein each $R^1$ is independently hydrocarbyl, or both hydrocarbyl groups $R^1$ may be joined to each other to form a cyclic anhydride. Examples of acyclic carboxylic anhydrides useful in the instant process are acetic anhydride, perfluorobutyric anhydride, trifluoroacetic anhydride, benzoic anhydride, hexanoic anhydride, and methacrylic anhydride. These acyclic anhydrides may also be so-called mixed anhydrides, such as acetic propanoic anhydride. In the case of mixed anhydrides, two N-acylimidazoles will be obtained, each derived from one of the acyl groups in the mixed anhydride. Symmetrical anhydrides (both $R^1$ groups the same) are preferred. A typical reaction of a CDI with an acyclic carboxylic anhydride is:

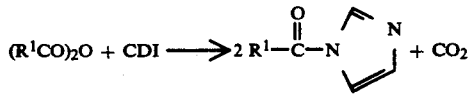

Cyclic anhydrides are also useful in the instant process. Examples of such cyclic anhydrides include, but are not limited to, succinic anhydride, maleic anhydride, phthalic anhydride, and itaconic anhydride. When a cyclic anhydride reacts with a CDI, a compound containing two N-acylimidazole groups will be produced (assuming only one anhydride group per cyclic anhydride molecule), since the anhydride groups are also connected by the cyclic structure. For example, reaction of phthalic anhydride with a CDI proceeds as follows:

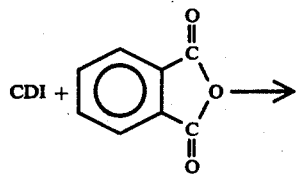

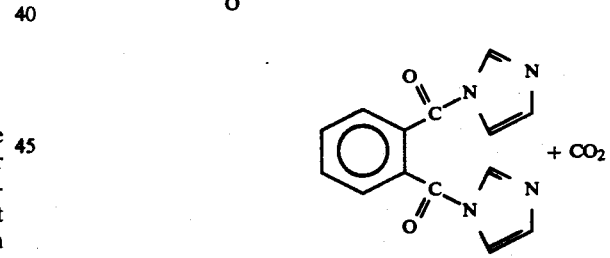

Examples of suitable substituents that may be present either in the carboxylic anhydride (for example, the group $R^1$) or in the 2, 4 or 5 positions of the imidazole ring of the CDI (and hence also present in the N-acylimidazole product), include, but are not limited to ether, ester, amide, fluoro, chloro, bromo, and iodo, and for substitution in the imidazole ring, hydrocarbyl. Any combination of substituents in any of these positions may be present.

The carboxylic anhydride may be part of a much larger molecule, such as a polymer. For example, the carboxylic anhydride may be maleic anhydride or itaconic anhydride that has been (usually free radically) copolymerized with other monomers, so that the anhydride group remains intact. The carboxylic anhydride may also contain more than one anhydride group, as in pyromellitic anhydride, or a plurality of anhydride groups as in the copolymers mentioned above. It is preferred if the anhydride groups in the copolymer are cyclic.

While virtually any ratio of the ingredients will yield the desired N-acylimidazoles, it is preferred if the ratio of total anhydride groups to the CDI is about 1. This insures the most efficient use of the starting materials, and obviates the need for removal of unreacted starting materials, i.e., yields relatively pure N-acylimidazole directly. Of course if it is desired to react only part of the anhydride groups (as in a polymer containing anhydride), less CDI would be used.

While temperature is not critical, convenient reaction rates are obtained at about 0° C. to about 200° C., preferably about 20° C. to about 100° C. The use of solvents is optional, and any solvent used should be aprotic. Solvents are particularly useful when the ingredients are not miscible or one or both of the ingredients are solid at the process temperature. A useful solvent is methylene chloride. Useful solvent types include halocarbons, esters, aromatics, etc. Protic solvents such as alcohols, water, primary and secondary amines should be avoided.

It is preferable to avoid water vapor, so the process is conveniently carried out under a blanket of nitrogen, argon, or $CO_2$. Agitation to achieve mixing of the ingredients is preferred.

The product N-acylimidazole may be used directly as made in the process, since the only byproduct is gaseous $CO_2$. If a solvent is used, it may be removed by distillation. The product N-acylimidazole may be purified by distillation or crystallization, as appropriate.

As described by H. A. Staab (supra, which is hereby included by reference), N-acylimidazoles are useful intermediates for the preparation esters, amides, peptides, carboxylic anhydrides, and other types of organic compounds. This reference also describes the preparation of CDIs.

In the following Examples, the CDI used is 1,1'-carbonyldiimidazole. All parts are parts by weight.

EXAMPLE 1

N-Acetylimidazole

Into 13 parts methylene chloride containing 1.86 parts carbonyldiimidazole, 1.14 parts acetic anhydride was slowly added. After 1 hour, the mixture became cloudy. The solvent was removed to obtain 2.37 parts crude acetylimidazole, from which 1.31 parts recrystallized product was obtained from toluene. $^1$H-NMR and melting point were consistent with authentic acetylimidazole.

EXAMPLE 2

N-Methacryloylimidazole

Into 39 parts methylene chloride containing 9.83 parts carbonyldiimidazole, 9.35 parts methacrylic anhydride was slowly added. Gas evolution began immediately; after 1 hour the slurried mixture became clear, and after 3 hours the gas evolution was complete. The solvent was removed to obtain 17 parts crude product. A 15 part fraction was distilled at 0.25 torr to obtain 6.9 parts of a material distilling from 44 to 60° C. IR, $^1$H-NMR, $^{13}$C-NMR were consistent with authentic material prepared by other routes (J. Polym. Sci., Polym. Chem. Ed., Vol. 12, pp. 2453-2455 (1974)).

EXAMPLE 3

N-benzoylimidazole

Into 132 parts methylene chloride containing 8.16 parts carbonyldiimidazole, 11.31 parts benzoic anhydride in 66 parts methylene chloride was added. The resulting mixture was refluxed 5 hours until gas evolution ceased. The yield after removal of solvent at reduced pressure was 19.31 parts crude material, demonstrated as predominantly benzoylimidazole by IR, GC-MS, $^1$H-NMR, and $^{13}$C-NMR accompanied by some dichloromethane. The compound is known, Chem. Ber., Vol. 95, pp. 1275-1283 (1961).

EXAMPLE 4

Polymeric N-Acylimidazole

Into a solution of 5.04 parts SMA-100 styrene/maleic anhydride copolymer (Atochem, Inc.) in 50 parts dichloromethane, there was added a slurry of 5.09 parts carbonyldiimidazole in 10.1 parts methylene chloride. The resulting mixture was refluxed for two hours. The solids dissolved, gas was generated, and the mixture turned a very deep red. The IR absorbances at 1780 and 1857 cm$^{-1}$ (SMA-1000) and 1754 cm$^{-1}$ (carbonyldiimidazole) were completely replaced in the product by absorbance peaks at 1758, 1780, and 1730 cm$^{-1}$.

EXAMPLE 5

N-Heptafluorobutyroylimidazole

Into a mixture of 10 parts perfluorobutyric anhydride in 40 parts of dichloromethane, there was added a slurry of 4.0 parts carbonyldiimidazole in 10.25 parts methylene chloride. The resulting mixture was refluxed for one hour. Gas generation was noted during the addition and reflux steps. The IR absorbances at 1798 and 1866 cm$^{-1}$ (anhydride) and 1754 cm$^{-1}$ (carbonyldiimidazole) were replaced in the product by a peak at 1754 cm$^{-1}$. The yield after removal of solvent by vacuum was 12.3 parts.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A process for the production of N-acylimidazoles, comprising, contacting a carboxylic anhydride with a carbonyldiimidazole.

2. The process as recited in claim 1 carried out in the presence of an aprotic solvent.

3. The process as recited in claim 1 carried out at a temperature of about 0° C. to about 200° C.

4. The process as recited in claim 3 carried out at a temperature of about 20° C. to about 100° C.

5. The process as recited in claim 2 carried out at a temperature of about 0° C. to about 200° C.

6. The process as recited in claim 1 wherein the ratio of carboxylic anhydride groups to carbonyldiimidazole is about 1.

7. The process as recited in claim 3 wherein the ratio of carboxylic anhydride groups to carbonyldiimidazole is about 1.

8. The process as recited in claim 1 wherein said carboxylic anhydride has the formula $R^1C(O)$—O—C-

(O)R$^1$, wherein each R$^1$ is independently hydrocarbyl, or both hydrocarbyl groups R$^1$ are joined to each other to form a cyclic anhydride.

9. The process as recited in claim 7 wherein said carboxylic anhydride has the formula R$^1$C(O)—O—C-(O)R$^1$, wherein each R$^1$ is independently hydrocarbyl, or both hydrocarbyl groups R$^1$ are joined to each other to form a cyclic anhydride.

10. The process as recited in claim 8 wherein each R$^1$ is the same.

11. The process as recited in claim 9 wherein each R$^1$ is the same.

12. The process as recited in claim 8 wherein said R$^1$ contains one or more substituents selected from the group consisting of ether, ester, amide, fluoro, chloro, bromo, and iodo.

13. The process as recited in claim 9 wherein said R$^1$ contains one or more substituents selected from the group consisting of ether, ester, amide, fluoro, chloro, bromo, and iodo.

14. The process as recited in claim 1 wherein said carboxylic anhydride is elected from the group consisting of acetic anhydride, perfluorobutyric anhydride, trifluoroacetic anhydride, benzoic anhydride, hexanoic anhydride, methacrylic anhydride, succinic anhydride, maleic anhydride, phthalic anhydride, and itaconic anhydride.

15. The process as recited in claim 7 wherein said carboxylic anhydride is elected from the group consisting of acetic anhydride, perfluorobutyric anhydride, trifluoroacetic anhydride, benzoic anhydride, hexanoic anhydride, methacrylic anhydride, succinic anhydride, maleic anhydride, phthalic anhydride, and itaconic anhydride.

16. The process as recited in claim 1 wherein said carbonyldiimidazole is 1,1'-carbonyldimidazole.

17. The process as recited in claim 2 wherein said aprotic solvent is methylene chloride.

18. The process as recited in claim 1 wherein said anhydride is a copolymer containing a plurality of cyclic anhydride groups.

19. The process as described in claim 9 wherein said carbonyldiimidazole is 1,1'-carbonyldiimidazole.

* * * * *